(12) United States Patent
Kinoshita et al.

(10) Patent No.: US 6,250,799 B1
(45) Date of Patent: Jun. 26, 2001

(54) THERMAL ANALYZING APPARATUS

(75) Inventors: Ryoichi Kinoshita; Nobutaka Nakamura, both of Chiba; Masatsugu Kawasaki, Hachioji, all of (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/482,805

(22) Filed: Jan. 13, 2000

(30) Foreign Application Priority Data

Jan. 14, 1999 (JP) .................................................. 11-008085

(51) Int. Cl.$^7$ .............................. G01N 25/00; F27D 7/06
(52) U.S. Cl. ................................................ 374/14; 373/111
(58) Field of Search .................................. 374/14, 43, 45; 219/483, 506; 373/109, 110, 111

(56) References Cited

U.S. PATENT DOCUMENTS

| 4,763,536 | * | 8/1988 | Beshoory | 374/14 |
| 5,669,554 | * | 9/1997 | Nakamura et al. | 374/14 |
| 5,869,810 | * | 2/1999 | Reynolds et al. | 373/111 |
| 6,159,543 | * | 12/2000 | Brifford | 427/250 |

* cited by examiner

Primary Examiner—Diego Gutierrez
Assistant Examiner—Yaritza Guadalupe
(74) Attorney, Agent, or Firm—Adams & Wilks

(57) ABSTRACT

An integral structure is formed having a downstream opening portion of the first furnace tube joined with a second cylindrical furnace tube side face. A structure is provided by a light transmissive window provided in the opening portions at respective ends of the second furnace tube, and a gas discharge section provided in at least one position in the second furnace tube side face.

5 Claims, 4 Drawing Sheets

THERMAL ANALYZING APPARATUS

BACKGROUND OF THE INVENTION

The present invention relates to a novel improvement of a thermal analyzing apparatus for examining change in temperature or time of a material physical property. More specifically, the invention relates to a novel improvement of a furnace tube structure of a thermal analyzing apparatus for measuring an evolved gas from a sample on a thermal analyzing apparatus by a Fourier transform infrared spectroscopic photometer.

Conventionally, an approach has been frequently practiced that an evolved gas from a sample within a thermal analyzing apparatus is analyzed by another gas analyzing apparatus. The thermal analyzing apparatuses for conducting this approach, in particular, often use a thermogravimetric measuring apparatus (hereinafter abbreviated as TG) while the evolved gas analyzing apparatuses often use a Fourier transform infrared spectroscopic photometer (hereinafter abbreviated as FT-IR), mass spectrometric apparatus, gas cromatograph mass spectrometric apparatus, etc. Among them, as a method for measuring an evolved gas from a sample within TG by FT-IR there is an apparatus having a structure, for example, as shown by R. Kinoshita et al., J. Thermal Anal., 38(1992)1891–1900. In this apparatus, an evolved gas from a sample within TG is introduced into a gas cell through a transfer line attached to a tip of a furnace tube. The IR light from FT-IR is incident through a window of the gas cell so that IR absorption is made due to the evolved gas introduced in the gas cell when IR light is passing trough the gas cell and IR absorption is detected by a downstream detector. The furnace tube, the transfer line and the gas cell are held in temperature for a purpose of prevention against condensation of the evolved gas. The heat insulation, in general, often uses 200° C.–300° C. The gas cell has a detailed structure, as shown by David A. C. Compton, David. J. Johnson, Research & Development, February (1989), having a heat insulation heater around a cylindrical metal tube and an IR transmissive window member (ZnSe and KBr) in a cylindrical opening. The evolved gas from the TG is introduced from a cylindrical metal tube side face through a transfer line, and discharged from a separately-provided discharge port. The IR light is incident from one opening of the metal tube through a window member, and outgoing through the window member in the other opening, being guided to a detector.

Also, in Nicolet FT-IR Technical Note TN-8714, there are shown a gas cell 46 with a structure as was shown in FIG. 4 and an interface to a TG furnace tube. The gas cell 46 is cylindrical and sealed at one opening by a reflection mirror 43 and at the other by a window member 42 transmissive of IR light so that an evolved gas from TG is introduced from a cylindrical gas cell 46 side face through an inlet line 44, and discharged through a gas discharge line 45 provided in the gas cell side face. The gas inlet line 44 is made of glass and connected to a top of a furnace tube by a glass ball joint. The gas cell main body is accommodated in a heat-insulated chamber 41 and held at a temperature of up to 325° C. as maximum.

There is real time property as one important point in TG/FT-IR measurement. That is, in order for a point that the evolved gas from a sample within TG is to be detected on an IR side with a time lag as low as possible, there is a necessity to introduce the evolved gas in TG into the gas cell as soon as possible. The methods for improving real time property include a method of reducing as low as possible a capacitance of a connection means from the TG side to the gas cell thereby decreasing a dead volume, and a method of increasing a flow rate of carrier gas to introduce as early as possible to the gas cell. However, the increase in flow rate of carrier gas results in decrease in concentration of the evolved gas within the gas cell, wherein decrease in absorption sensitivity is observed and hence excessive increase is not desired. Accordingly, generally taken is a method of reducing a dead volume as low as possible in the connection means. Because the conventional examples in either case is to reduce a dead volume in the connection means as low as possible, the TG furnace tube and gas cell are connected using a thin tubular connection means such as a transfer line, inlet line or the like. Also, furthermore, heat insulation is conducted in both the connection means and the gas cell for the purpose of preventing against gas condensation.

However, the thin tubular connection means is comparatively difficult to evenly keep temperature and liable to form temperature distribution. Accordingly, there is a case that a cold spot is formed that is lower than an objective heat insulation as the case may be. In particular, the connection part with the furnace tube or gas cell connects between different formed parts and hence difficult to conduct heat insulation, readily turned to a cold spot. In some measurements there are cases a gas with a high boiling point is evolved to be possibly condensed at a cold spot. There is a defect that, once condensation occurs, the flow passage is narrowed and hence evolved-gas blockage becomes more ready to occur finally blocking the flow passage completely.

Although in order to prevent condensation of an evolved gas with a high boiling point there is a method of heat insulation at a higher temperature, in conventional examples a maximum temperature is around 325° C. at the most. Because the conventional example transfers the gas using a thin tubular connection means, enclosure property is required to a gas cell discharge port and seal members are used also in the window portions of the connection part and gas cell. However, the raise of temperature causes a problem of heat resistance of the seal member and a problem of weakening sealability, having a defect of not suited for heat insulation at excessively high temperature.

Recently, in analyzing dust-incineration evolved gases from incinerators there is a desire of identifying substances that are not in a gaseous state unless at a high temperature close to 500° C. However, in the conventional example TG/FT-IR system there is a defect that heat insulation is difficult at 500° C. and hence nothing is coped with.

It is a problem of the present invention to provide a thermal analyzing apparatus which is capable of insulating heat at a high temperature of 500° C. and higher without spoiling real-time property and free from blockage in flow path due to condensation of an evolved gas.

SUMMARY OF THE INVENTION

The invention comprises: a first cylindrical furnace tube forming a closed space around a sample, a first heating means for heating the furnace tube, a carrier gas for transferring an evolved gas from the sample from upstream to downstream, a second cylindrical furnace tube, a second heating means for heating the second furnace tube, an integral structure having a downstream opening portion of the first furnace tube joined with a second cylindrical furnace tube side face, a light transmissive window provided in the opening portions at respective ends of the second furnace tube, and a gas discharge section provided in at least one position in the second furnace tube side face.

[Operation]

The carrier gas flowed from the downstream opening portion of the first furnace tube and the evolved gas from the sample are passed through an inside of the second furnace tube and discharged to an outside from the gas discharge section provided in the second furnace tube side face. The first furnace tube heats up the sample similarly to the conventional thermal analyzing apparatus furnace tube, and discharges the evolved gas by the carrier gas to a downstream side. On the other hand, the second furnace tube introduces the evolved gas from the first furnace tube, and performs a function of a conventional gas cell by incident IR light from opening portions at one end and outgoing IR light through the other end.

DETAILED DESCRIPTION OF THE INVENTION

Figure 1:
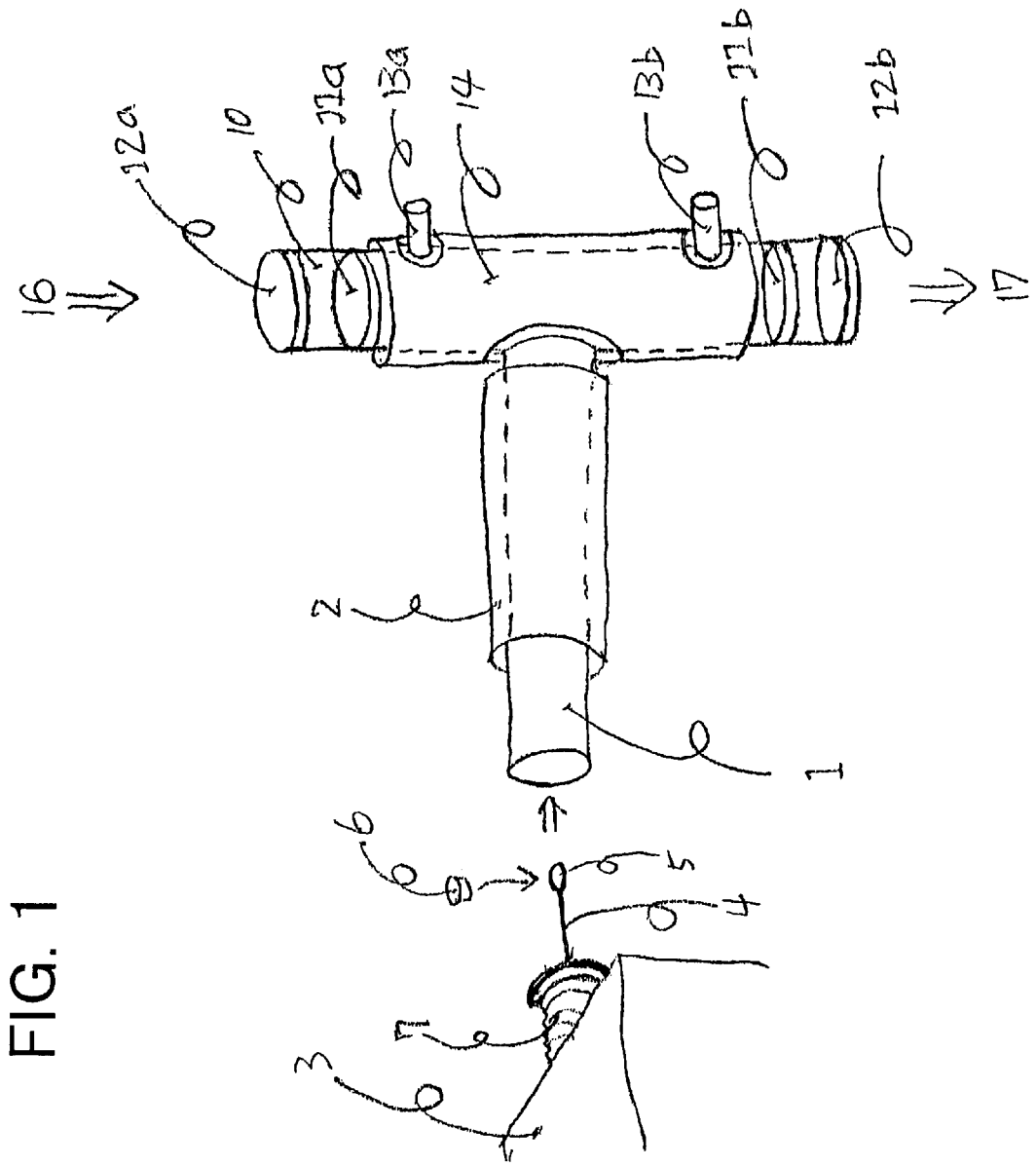
FIG. 1 is a structural view of an embodiment of the present invention

FIG. 1 shows an embodiment of the present invention. 1 is a first cylindrical furnace tube made of ceramic alumina or heat resistive metal such as inconel, around which is placed a heating furnace 2 to heat the first furnace tube. The heating furnace 2 is heated by a temperature controller for a thermal analyzing apparatus according to a proper temperature program. 3 is a measuring section of a thermogravimetric measuring apparatus. 4 is a balance beam of a thermogravimetric measuring apparatus. 5 is a holder attached to the balance beam 4. A sample is put in a sample vessel 6 and thereafter rested on the holder 5. By moving the thermogravimetric measuring apparatus 3 through a moving mechanism, the balance beam 4 rested thereon with the sample vessel 6 is inserted into the first furnace tube 1. During insertion, the first furnace tube 1 at its balance beam side opening is enclosed by close contact with a bellows mechanism 7 attached to a measuring section of the thermogravimetric measuring apparatus 3. The thermogravimetric measuring apparatus 3 measures a weight change of the sample rested on the holder 5, and measure a temperature of the holder 5 as a sample temperature by a thermocouple inserted in the balance beam 4. Also, by temperature controlling the heating furnace 2, the sample temperature within the first furnace tube can be controlled. On the other hand, carrier gas is flowed from a thermogravimetric measuring apparatus 3 side (upstream), which flow through an inside of the first furnace tube.

Figure 2:
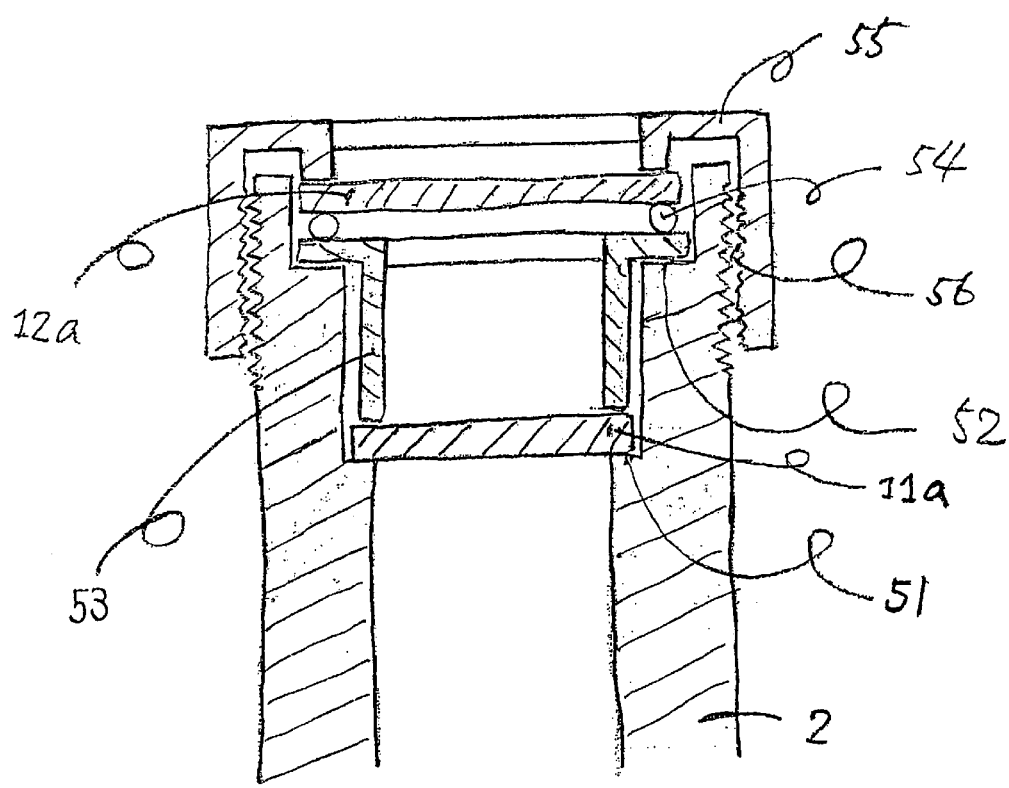
FIG. 2 is a sectional view of a second furnace tube opening.

The first furnace tube at its downstream opening is joined to a side surface of a second cylindrical furnace tube 10 made of a same material as the first furnace tube. Thus, the first furnace tube and the second furnace tube forms an integral structure in a T-character form. 11a, 11b are ZnSe discs of IR light transmissive member and arranged at somewhat inner positions of opposite end openings of the second furnace tube. 12a, 12b are ZnSe discs of IR light transmissive member and sealed using a seal member at opposite end openings of the second furnace tube. 13a, 13b are gas discharge ports placed on a side surface of the second furnace tube and arranged at inner positions than the inner ZnSe 11a, 11b. 14 is a heating furnace surrounding the second furnace tube and controls heating the furnace tube at between the inner ZnSe discs 11a and 11b. The heating furnace 14 may be connected to the temperature controller for the thermogravimetric analyzing apparatus and controlled similarly to the heating furnace 2, or independently connected to another temperature controller and controlled of temperature according to a proper program. FIG. 2 shows a detail of arrangement and sealing of the ZnSe discs 11a, 11b and 12a, 12b on the second furnace tube. FIG. 2 shows a sectional view of the second furnace tube at one opening. The furnace tube section has two steps 51, 52. On the inner step 51 the inner ZnSe disk 11a is placed and held from above by a flanged holding ring 53. The flange of the holding ring 53 contacts the outer step 52. The outer ZnSe disk 12a is placed on an O-ring 54 placed on the flange of the holding ring 53. A thread 56 is made in an outer periphery of the opening of the second furnace tube, and in mesh with a thread of the holder 55. By tightening this screw, the O-ring 54 is pressed through the outer ZnSe disk 12a whereby the second furnace tube at its opening is sealed.

Next explained a analyzing method on evolved gas in this embodiment. First the heating furnace 14 is controlled to a constant temperature (e.g. 500° C.) using the separate temperature controller. From FT-IR incident infrared (IR) light 16 is introduced from above of the second furnace tube by using a mirror, etc., and drawn as outgoing IR light 17 from an opposite side through an inside of the second furnace tube. The outgoing TR light 17 is returned again to the detector on the FT-IR side by using a mirror, etc. Due to this, the second furnace tube functions as a temperature-controlled gas cell.

A sample is put in the sample vessel 6 as already stated and rested on the holder 5, being placed within the first furnace tube. As a carrier gas, nitrogen gas of 200mi/mn. is introduced from a side of the thermogravimetric measuring apparatus 3, which passes through an inside of the first furnace tube, enters from a side surface of the second furnace tube, passes through the inside of the second furnace tube and is discharged from the gas discharge ports 13a and 13b. Next, the sample is heated by the furnace 2 with the temperature controller of the thermogravimetric measuring apparatus. If the sample starts to decompose or so at a certain temperature and gas is evolved from the sample, the thermogravimetric measuring apparatus detects a weight change of the sample due to gas evolvement. On the other hand, the evolved gas is introduced by the carrier nitrogen gas from the first furnace tube directly to the second furnace tube. The second furnace tube functions as a gas cell, and IR absorption of the evolved gas is detected by the FT-IR detector.

In the apparatus of this structure, if the evolved gas is discharged from the first furnace tube corresponding to a furnace tube of the conventional thermogravimetric analyzing apparatus, it is almost simultaneously introduced into the second furnace tube corresponding to the conventional gas cell. Accordingly, there is almost no time lag and the nature of real time is sufficiently secured. Also, because of a structure that has no thin and long tubular connection means as in the conventional and is joined of the furnace tube and the gas cell into one body, there is almost tree of cold spots in the connection portion liable to be a problem in the conventional. Also, because the first furnace tube with an inner diameter as it is joined to the second furnace tube (gas cell), even it an evolved gas with a high boiling point condenses in the vicinity of the joint portion, there is no possibility that the flow passage is narrowed and clogged as encountered in the conventional.

Furthermore, it is possible for this example to perform heat insulation at 500° C. difficult in the conventional. First, the joint portion of the furnace gas tube and the gas cell is in an integral structure and hence does not require a seal member, free of a problem with heat resistance. Next, because of no use of a passage in a thin tubular form as used in the conventional, a gas is allowed to flow even if air-tightness to the gas cell discharge port is not high as that of the conventional. Due to this, as was shown in FIG. 2 of the embodiment, the inner ZnSe discs 11a, 11b if not made by a strict seal member can fully define produce as flow and discharge it from the discharge port. This makes it possible for the second furnace tube corresponding to a gas cell to raise and keep the temperature to around a heat resistive temperature of a window material itself. Znse is used in the embodiment, and it is usable even at 500° C. according to our evaluation test of the heat resistance. Furthermore, in the embodiment, the outer ZnSe disc 12a, 12b use an O-ring for sealing as shown in FIG. 2 to increase the air tightness of the second furnace tube. The outer ZnSe disk 12a, 12b can be placed distant from the inner ZnSe disk 11a, 11b, and which has no problem if an O-ring as a seal member is used. Also, by making in the double window members, the inner window member has also a heat insulation effect, which also has an effect to prevent the window member itself from becoming a cold spot.

Also, the explanation on the evolved gas analyzing method was made using an example that the second furnace tube is controlled at a constant temperature. However, it is possible to use the temperature controller of the thermal analyzing apparatus to control temperature of the second furnace tube according to a similar program to the temperature control of the first furnace tube. If this method is conducted, an evolved gas is prevented from condensing but there is no possibility that the evolved gas in a low temperature region is directly introduced to the second furnace tube (gas cell) at 500° C., providing an effect of preventing against secondary decomposition in a gas cell of the evolved gas.

Figure 3:
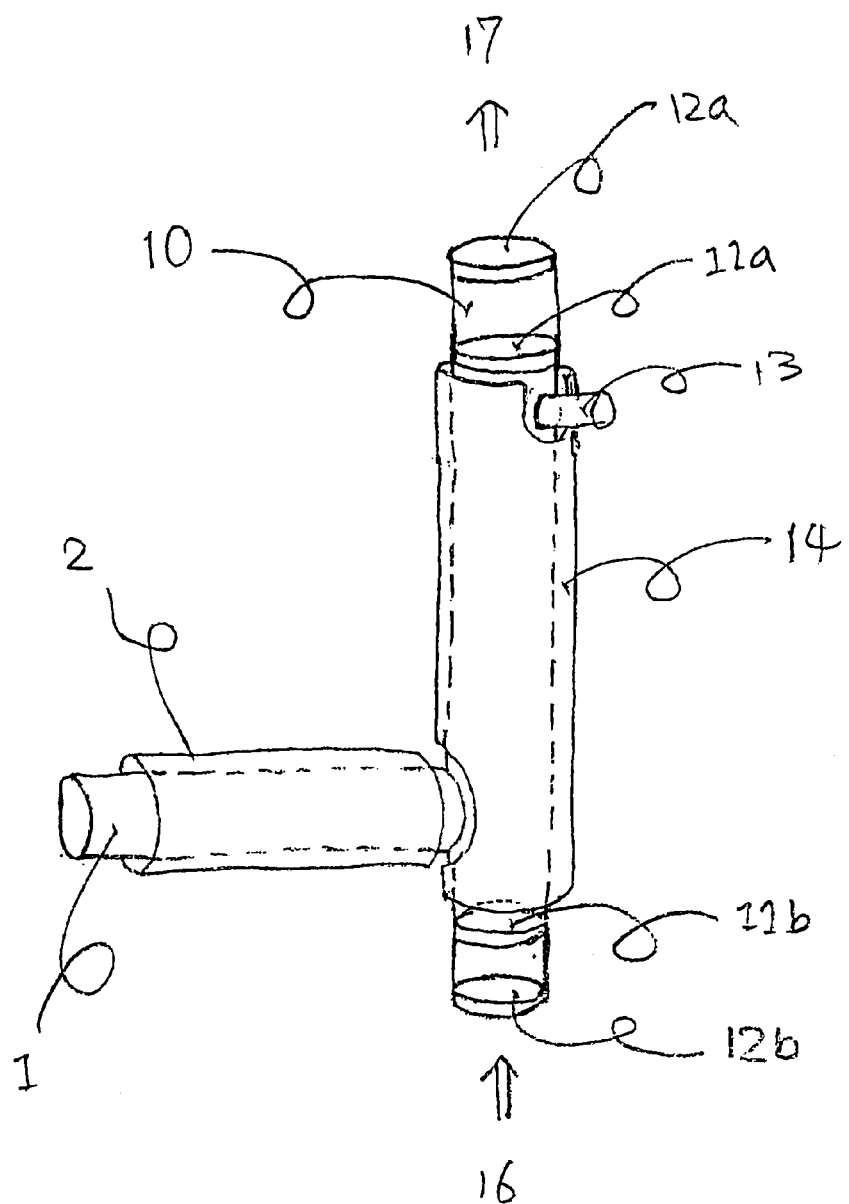
FIG. 3 is a structural view of an embodiment structured in an L-character form.
Figure 4:
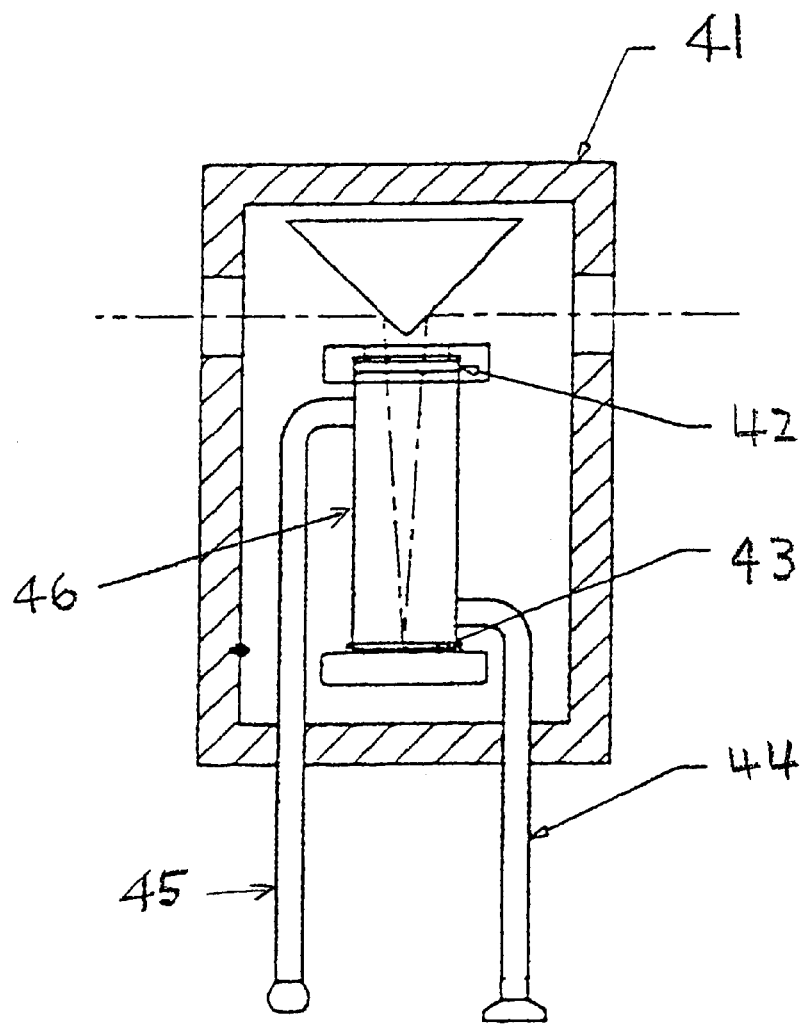
FIG. 4 is a gas cell structure of a conventional example.

FIG. 3 is a structure of another embodiment wherein a first furnace tube has an opening joined to a side surface lower portion of a second furnace tube, providing a structure in an L-character form. In this case, a gas discharge port is provided one at an upper portion. The flow of a carrier gas is in one direction of from the opening of the first furnace tube to the gas discharge port at the upper portion of the second furnace tube, differently from the FIG. 1 example. In this case, the gas flow also becomes convection within the second furnace tube and becomes more smooth.

Although the embodiment explained with the second furnace tube arranged in a vertical direction, where IR light is passed in a horizontal direction the second furnace tube may be arranged in the horizontal direction.

Also, the diameter and length of the second furnace tube are not undergo restriction and may be set in proper dimensions. This provides a merit that, for example where the sensitivity of IR absorption is insufficient, the second furnace tube is increased in length to increase an IR optical path thereby obtaining increase of IR sensitivity.

Also, although in the embodiment explanation was made on the horizontal type thermogravimetric measuring apparatus as a thermal analyzing apparatus, even if a thermogravimetric measuring apparatus of a hung-down type or up-dish type, it is needless to say that a structure constructed similarly to the embodiment is possible by vertically arranging the first furnace tube. Also, a similarly structured apparatus to the present embodiment can be structured for an apparatus for conducting differential thermal analysis simultaneous with differential type TG using two balance beams on sample and reference sides. Furthermore, in a thermal analyzing apparatus having other structure than a thermogravimetric measuring apparatus, e.g. a differential scanning calorimeter or thermomechanical analyzer, it is possible to provide a structure that analysis can be made on an evolved gas simultaneous with each analysis by putting a sample setting section in the first furnace tube.

A structure is provided that comprises: a first cylindrical furnace tube forming a closed space around a sample, a first heating means for heating the furnace tube, a carrier gas for transferring an evolved gas evolved from the sample from upstream to downstream, a second cylindrical furnace tube, a second heating means for heating the second furnace tube, an integral structure having a downstream opening portion of the first furnace tube joined with a second cylindrical furnace tube side face, a light transmissive window provided in the opening portions at respective ends of the second furnace tube, and a gas discharge section provided in at least one position in the second furnace tube side face. Due to this, when an evolved gas is discharged from the first furnace tube corresponding to a conventional thermal analyzing apparatus furnace tube, it is introduced almost simultaneously to the second furnace tube corresponding to a conventional gas cell. Accordingly, there is an effect that thermal analysis and evolved gas analysis can be conducted without spoiling real-time property in evolved gas detection. Also, there is an effect that high temperature heat insulation is possible at 500° C. and higher because heat resistance is not restricted by the joining part or seal member. Also, Because no thin, long connection portion is provided as given in the conventional, an effect was obtained that no blockage of a flow passage occurs due to evolved gas condensation.

What is claimed is:

1. A thermal analyzing apparatus, characterized by having a structure comprising: a first cylindrical furnace tube forming a closed space around a sample, a first heating means for heating the furnace tube, a carrier gas for transferring a gas evolved from the sample from upstream to downstream, a second cylindrical furnace tube, a second heating means for heating the second furnace tube, an integral structure having a downstream opening portion of the first furnace tube joined with a second cylindrical furnace tube side face, a light transmissive window provided in the opening portions at respective ends of the second furnace tube, and a gas discharge section provided in at least one position in the second furnace tube side face, wherein the carrier gas flowed from the downstream opening portion of the first furnace tube and the evolved gas from the sample are passed through an inside of the second furnace tube and discharged to an outside from the gas discharge section provided in the second furnace tube side face.

2. A thermal analyzing apparatus according to claim 1, wherein the integral structure joined with the downstream opening portion of the first furnace tube and the second cylindrical furnace tube side face has a T-character or L-character form.

3. A thermal analyzing apparatus according to claim 1 wherein the first heating means and the second heating means are structured to be temperature-controlled according to a same temperature program.

4. A thermal analyzing apparatus according to claim 1, wherein the second heating means has a function of controlling to a constant temperature of not exceeding a heat resistance temperature of the light transmissive window member provided in the opening potion of the second furnace tube.

5. A thermal analyzing apparatus according to claim 1, wherein first furnace tube and the second furnace tube are structured of a metal material having heat resistance.

* * * * *